(12) United States Patent
Lee et al.

(10) Patent No.: US 10,575,761 B2
(45) Date of Patent: Mar. 3, 2020

(54) METHOD AND APPARATUS FOR RECOGNIZING GAIT MOTION

(71) Applicant: Samsung Electronics Co., Ltd., Suwon-si, Gyeonggi-do (KR)

(72) Inventors: Jusuk Lee, Hwaseong-si (KR); Kyung-Rock Kim, Yongin-si (KR); Kee Hong Seo, Seoul (KR); Youngbo Shim, Seoul (KR); Sunghwan Ahn, Seoul (KR); Bokman Lim, Yongin-si (KR); Jun-Won Jang, Seoul (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 212 days.

(21) Appl. No.: 14/681,847

(22) Filed: Apr. 8, 2015

(65) Prior Publication Data

US 2016/0095538 A1 Apr. 7, 2016

(30) Foreign Application Priority Data

Oct. 7, 2014 (KR) ........................ 10-2014-0134853

(51) Int. Cl.
*A61B 5/11* (2006.01)
*A61H 3/00* (2006.01)
*G06K 9/00* (2006.01)

(52) U.S. Cl.
CPC ............... *A61B 5/112* (2013.01); *A61H 3/00* (2013.01); *A61H 2201/1628* (2013.01); *A61H 2201/50* (2013.01); *G06K 9/00348* (2013.01)

(58) Field of Classification Search
CPC .............. A61H 3/00; A61H 2201/5061; A61H 2201/5079; A61H 2201/5069;
(Continued)

(56) References Cited

U.S. PATENT DOCUMENTS

2004/0130620 A1* 7/2004 Buehler ............. G06K 9/00335
348/143
2004/0249316 A1* 12/2004 Ashihara ............. A61B 5/1038
600/595
(Continued)

FOREIGN PATENT DOCUMENTS

JP 10277969 A 10/1998
JP 2006192276 A 7/2006
(Continued)

OTHER PUBLICATIONS

Ngo Thanh Trung et al., "Inertial-sensor-based Walking Action Recognition using Robust Step Detection and Inter-class Relationships", 21st International Conference on Pattern Recognition, Nov. 2012, pp. 3811-3814.
(Continued)

*Primary Examiner* — Patrick Fernandes
(74) *Attorney, Agent, or Firm* — Harness, Dickey & Pierce, P.L.C.

(57) ABSTRACT

A method and apparatus for recognizing a gait motion are provided. The apparatus may set a gait motion recognition period based on measured right and left hip joint angle information, may input, to a trained neural network, right and left hip joint angle information and vertical acceleration information measured during the gait motion recognition period, and may recognize a gait motion.

20 Claims, 9 Drawing Sheets

(58) Field of Classification Search
CPC ..... A61H 2201/1628; A61H 2201/501; G06K 9/00348
See application file for complete search history.

(56) References Cited

U.S. PATENT DOCUMENTS

| | | |
|---|---|---|
| 2009/0192414 A1 | 7/2009 | Yasuhara |
| 2010/0234775 A1 | 9/2010 | Yasuhara et al. |
| 2011/0061697 A1* | 3/2011 | Behrenbruch ........... A45B 3/00 135/66 |
| 2012/0215140 A1* | 8/2012 | Hirata .................. A61H 1/0244 601/35 |
| 2013/0311133 A1* | 11/2013 | Kordari .................. G06F 17/10 702/160 |

FOREIGN PATENT DOCUMENTS

| | | |
|---|---|---|
| JP | 2007160076 A | 6/2007 |
| JP | 2013070785 A | 4/2013 |
| KR | 100802533 B1 | 2/2008 |
| KR | 20110082394 A | 7/2011 |
| KR | 20110083144 A | 7/2011 |
| KR | 101242517 B1 | 3/2013 |
| KR | 20140005415 A | 1/2014 |

OTHER PUBLICATIONS

Kamiar Aminian et al., "Estimation of Speed and Incline of Walking Using Neural Network", IEEE Transactions on Instrumentation and Measurement, vol. 44, No. 3, Jun. 1995, pp. 743.

* cited by examiner

METHOD AND APPARATUS FOR RECOGNIZING GAIT MOTION

CROSS-REFERENCE TO RELATED APPLICATION

This application claims the priority benefit of Korean Patent Application No. 10-2014-0134853, filed on Oct. 7, 2014, in the Korean Intellectual Property Office, the disclosure of which is incorporated herein by reference in its entirety.

BACKGROUND

1. Field

Some example embodiments relate to an apparatus and method for recognizing a gait motion, and more particularly, to an apparatus and method for recognizing a gait motion based on biometric data of a user sensed and/or measured by, for example, a walking assistance apparatus.

2. Description of the Related Art

Human walking is performed based on different operating mechanisms of the hip joints for each gait motion, for example, level walking, walking up stairs, walking down stairs, walking up a slope, or walking down a slope.

When a walking assistance apparatus is unable to recognize a gait motion of a user while assisting the walking of the user, a walking assistance optimized for each gait motion may not be provided. For example, when the walking assistance apparatus is unable to recognize a gait motion of the user, the walking assistance apparatus may only assist walking by collectively generating an oscillator-based pattern for each gait motion.

Accordingly, it is desired to recognize a gait motion of a user when human walking is to be assisted by, for example, a walking assistance apparatus. The walking assistance apparatus may operate differently based on operating mechanisms for each of recognized gait motions, thereby providing an optimized walking assistance.

SUMMARY

Some example embodiments relate to a method of recognizing a gait motion.

In some example embodiments, the method may include setting a gait motion recognition period based on measured right and left hip joint angle information, and recognizing a gait motion as walking down stairs, when a vertical acceleration value at a desired first point in vertical acceleration information, the vertical acceleration information including at least one vertical acceleration value measured during the gait motion recognition period, is equal to or greater than a first threshold. Information based on the results of the setting and recognizing may be provided to a walking assistance apparatus to improve the assistance provided by the walking assistance apparatus to a user.

The method may further include resampling data of right and left hip joint angle information and the vertical acceleration information in accordance with a data format when the vertical acceleration value is less than the first threshold, the right and left hip joint angle information being measured during the gait motion recognition period. Information based on the results of the resampling may be provided to the recognition unit.

The method may further include recognizing the gait motion as either walking down a slope or level walking, by inputting the resampled data to a trained neural network.

The method may further include recognizing the gait motion as walking up stairs, when the gait motion is not recognized as walking down a slope or level walking through the neural network, and when a value of a rotational speed in a forward direction at a desired second point in rotational speed information, the rotational speed information including rotational speed values in the forward direction measured during the gait motion recognition period, is equal to or greater than a second threshold.

The method may further include recognizing the gait motion as walking up a slope, when the gait motion is not recognized as walking down a slope or level walking through the neural network, and when a value of a rotational speed in a forward direction at a desired second point in rotational speed information, the rotational speed information including rotational speed values in the forward direction measured during the gait motion recognition period, is less than a second threshold.

The setting may include setting the gait motion recognition period, using a finite state machine (FSM), the FSM including states based on a gait cycle.

A transition condition between the states may be set based on right and left hip joint angles or right and left hip joint angular velocities at points.

Some example embodiments relate to a method of recognizing a gait motion.

In some example embodiments, the method may include setting a gait motion recognition period based on measured right and left hip joint angle information, and recognizing a gait motion by inputting right and left hip joint angle information and vertical acceleration information to a trained neural network, the right and left hip joint angle information and the vertical acceleration information being measured during the gait motion recognition period. Information based on the results of the setting and recognizing may be provided to a walking assistance apparatus to improve the assistance provided by the walking assistance apparatus to a user.

The method may further include resampling data of the right and left hip joint angle information and the vertical acceleration information in accordance with a data format. Information based on the resampling may be provided to the recognition unit.

The setting may include setting the gait motion recognition period using an FSM, the FSM including states based on a gait cycle.

A transition condition between the states may be based on right and left hip joint angles or right and left hip joint angular velocities.

The gait motion may include level walking, walking up stairs, walking down stairs, walking up a slope, and walking down a slope.

Some example embodiments relate to an apparatus for recognizing a gait motion.

In some example embodiments, the apparatus may include a setting unit configured to set a gait motion recognition period based on measured right and left hip joint angle information, and a recognition unit configured to recognize a gait motion as walking down stairs, when a vertical acceleration value at a desired first point in vertical acceleration information, the vertical acceleration information including at least one vertical acceleration value measured during the gait motion recognition period, is equal to or greater than a first threshold. The recognition unit may be configured to provide information based on results of the setting and recognizing to a walking assistance apparatus to improve the assistance provided by the walking assistance apparatus to a user.

The apparatus may further include a resampling unit configured to resample data of right and left hip joint angle information and the vertical acceleration information in accordance with a data format, when the vertical acceleration value is less than the first threshold, the right and left hip joint angle information being measured during the gait motion recognition period. The resampling unit may be configured to provide information based on the resampling to the recognition unit.

The recognition unit may be configured to recognize the gait motion as either walking down a slope or level walking, by inputting the resampled data to a trained neural network.

The recognition unit may be configured to recognize the gait motion as walking up stairs, when the gait motion is not recognized as walking down a slope or level walking through the neural network, and when a value of a rotational speed in a forward direction at a desired and/or preset second point in rotational speed information, the rotational speed information including rotational speed values in the forward direction measured during the gait motion recognition period, is equal to or greater than a second threshold.

The recognition unit may be configured to recognize the gait motion as walking up a slope, when the gait motion is not recognized as walking down a slope or level walking through the neural network, and when a value of a rotational speed in a forward direction at a desired and/or preset second point in rotational speed information, the rotational speed information including rotational speed values in the forward direction measured during the gait motion recognition period, is less than a second threshold.

The setting unit may be configured to set the gait motion recognition period, using an FSM including states based on a gait cycle.

A transition condition between the states may be set based on right and left hip joint angles or right and left hip joint angular velocities.

Additional aspects of some example embodiments will be set forth in part in the description which follows and, in part, will be apparent from the description, or may be learned by practice of the disclosure.

BRIEF DESCRIPTION OF THE DRAWINGS

The foregoing and other features of some example embodiments will be apparent from the more particular description of the non-limiting embodiments, as illustrated in the accompanying drawings in which like reference characters refer to like parts throughout the different views. The drawings are not necessarily to scale, emphasis instead being placed upon illustrating principles of some example embodiments. In the drawings.

DETAILED DESCRIPTION

Figure 1:
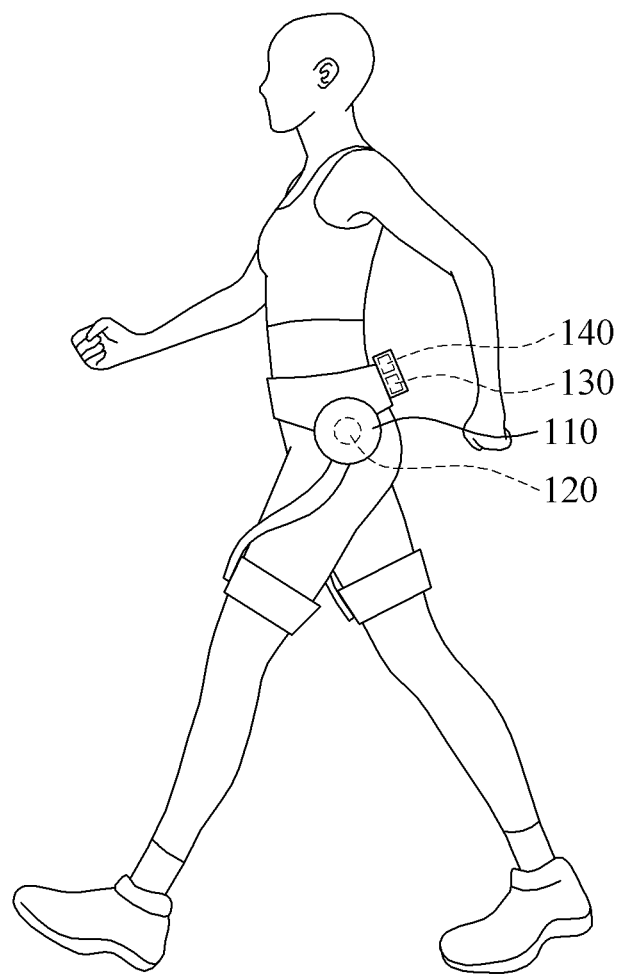
FIG. 1 illustrates a user wearing a walking assistance apparatus according to some example embodiments.

Example embodiments will now be described more fully with reference to the accompanying drawings, in which some example embodiments are shown. Example embodiments, may, however, be embodied in many different forms and should not be construed as being limited to the embodiments set forth herein; rather, these example embodiments are provided so that this disclosure will be thorough and complete, and will fully convey the scope of example embodiments to those of ordinary skill in the art. In the drawings, the thicknesses of layers and regions are exaggerated for clarity. Like reference characters and/or numerals in the drawings denote like elements, and thus their description may be omitted.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, terms used herein are selected from general terms being used in the related arts. Yet, the meanings of the terms used herein may be changed depending on a change and/or development of technologies, a custom, or preference of an operator in the art. Accordingly, the terms are merely examples to describe the example embodiments, and should not be construed as limited to the technical idea of the example embodiments.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Various example embodiments will now be described more fully with reference to the accompanying drawings in which some example embodiments are shown. In the drawings, the thicknesses of layers and regions are exaggerated for clarity.

FIG. 1 illustrates a user wearing a walking assistance apparatus according to some example embodiments.

Referring to FIG. 1, the walking assistance apparatus may include a driver 110, a sensor 120, an inertial measurement unit (IMU) sensor 130, and a controller 140. FIG. 1 illustrates an example of a hip-type walking assistance apparatus, however, there is no limitation thereto. Accordingly, the walking assistance apparatus may be applicable to, for example, a walking assistance apparatus for supporting an entire pelvic limb, or a walking assistance apparatus for supporting a portion of a pelvic limb. Also, the walking assistance apparatus may be applicable to, for example, any type of walking assistance apparatus for assisting the walking of a user, for example, a walking assistance apparatus for supporting a portion of a pelvic limb, a walking assistance apparatus for supporting up to a knee, and a walking assistance apparatus for supporting up to an ankle. Furthermore, it is obvious to one of ordinary skill in the art that the walking assistance apparatus may be applicable to an apparatus for assisting the physical rehabilitation of a user.

Additionally, while the assistance apparatus is referred to as a walking assistance apparatus in accordance with discussion of the example embodiments, the example embodiments presented herein are not limited thereto and may also be applied to other types or forms of physical assistance apparatuses, such as apparatuses designed to assistance a user's arm movements and/or functionality, or apparatuses designed to provide additional physical strength to a user's movements. Further, while the example embodiments are discussed in reference to use by a human being, one of ordinary skill in the art would appreciate that the example embodiments disclosed herein may also be applied to other beings and/or objects, such as animals, machines and/or robots, including surgical robots, assembly line/industrial robots, or autonomous robots.

The driver 110 may provide a user with motion assistance and may be disposed on, for example, a right hip portion and a left hip portion of the user. The sensor 120 may measure hip joint angle information for either and/or both hip joints of the user while the user is walking. The sensor 120 may be disposed in the driver 110. The hip joint angle information sensed and/or measured by the sensor 120 may include, for example, at least one of angles of either and/or both hip joints, a difference between the angles of both hip joints, and motion directions of either and/or both hip joints. In some example embodiments, the hip joint angle information may be referred to as "right and left hip joint angle information."

The IMU sensor 130 may measure acceleration information, rotational speed information, and the like while the user is walking. A gait motion of a user may be recognized based on the acceleration information and the rotational speed information measured by the IMU sensor 130 and the hip joint angle information measured by the sensor 120.

The controller 140 may set a gait motion recognition period based on right and left hip joint angle information. Vertical acceleration information and right and left hip joint angle information measured during the gait motion recognition period may be input to a neural network, and a gait motion may be recognized.

The controller 140 may recognize the gait motion of the user as described above, and may output a control signal to control the driver 110. Based on the control signal output from the controller 140, the driver 110 may provide the user with motion assistance suitable for the recognized gait motion.

Figure 2:
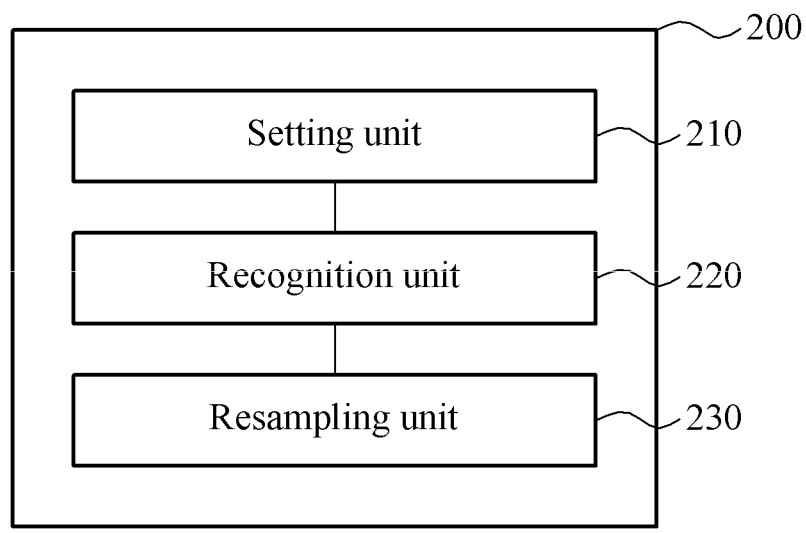
FIG. 2 is a block diagram illustrating a configuration of an apparatus for recognizing a gait motion according to some example embodiments.

FIG. 2 is a block diagram illustrating a configuration of an apparatus 200 for recognizing a gait motion according to some example embodiments.

Referring to FIG. 2, the apparatus 200 may include a setting unit 210, a recognition unit 220, and a resampling unit 230.

The setting unit 210 may set a gait motion recognition period based on right and left hip joint angle information. The right and left hip joint angle information may be measured by a sensing unit, which may be, for example, but is not limited to an encoder. Acceleration information data and rotational speed information data may be measured by a sensing unit, which may be, for example, but is not limited to an IMU sensor. The setting unit may also include a processor and memory for the processing of the information and data sensed and/or measured by the sensing unit. Additionally, the setting unit may use processors included in the recognition unit 220, resampling unit 230, or the walking assistance apparatus for the processing of the information and data sensed and/or measured by the sensing unit.

Right and left hip joint angle information data, acceleration information data and rotational speed information data measured to recognize a gait motion of a user may need to be equally divided. The gait motion recognition period may refer to a period used to recognize a gait motion of a user, and a user's motion may be recognized based on data measured during a set gait motion recognition period. The gait motion recognition period may be set for each step or stride.

The setting unit 210 may set the gait motion recognition period using a finite state machine (FSM), the FSM including states based on a gait cycle. The FSM may be executed on a processor and memory within the setting unit. A transition condition between the states in the FSM may be set based on right and left hip joint angles and/or right and left hip joint angular velocities at points at which the right and left hip joint angles and/or the right and left hip joint angular velocities cross.

Based on the above-described transition condition, the states in the FSM may be classified as, for example, a state in which a left leg swings while a right leg remains standing, a state in which a left leg swinging while a right leg remains standing lands, a state in which a right leg swings while a left leg remains standing, and a state in which a right leg swinging while a left leg remains standing lands.

The states in the FSM may be based on the gait cycle and the transition condition. In an example, every time a state transition is performed four times, a gait motion recognition period may be set for each stride. In another example, every time a state transition is performed twice, a gait motion recognition period may be set for each step.

However, the gait motion recognition period may not need to be set for each stride or step. For example, based on a user's settings, the gait motion recognition period may be set every time a state transition is performed once, twice, or three times, etc.

The FSM used to set a gait motion recognition period, the transition condition and the states of the FSM are merely examples to describe a method of setting a gait motion recognition period and there is no limitation thereto. The gait motion recognition period may be set as an arbitrary period in which data required to recognize a gait motion of a user is to be measured. An example of setting a gait motion recognition period will be further described with reference to FIGS. 3 and 4. The results of the data measured during the gait motion recognition period may then be provided to the recognition unit 220.

The recognition unit 220 may recognize the gait motion by inputting right and left hip joint angle information and vertical acceleration information measured during the set gait motion recognition period to a trained neural network.

The gait motion may include, for example, level walking, walking up stairs, walking down stairs, walking up a slope, and walking down a slope. Hereinafter, level walking, walking up stairs, walking down stairs, walking up a slope and walking down a slope are merely examples of the gait motion for description of some example embodiments, and there is no limitation thereto. For example, the gait motion may include subdivided motions, and may further include motions with different operating mechanisms of hip joints for a standing state, a state in which a user is sitting down, or a state in which a user is standing up.

The neural network may refer to an algorithm generated by modeling a human brain cell structure in engineering and imitating a human training ability to solve a problem of classifying an input pattern as a desired (or, alternatively predetermined) group. The neural network may classify and output an input pattern as a desired (or, alternatively predetermined) group through a training process. The neural network may be implemented, for example, on a computer or data processing system comprising one or more processors, memory and storage, and may also be implemented on a distributed computing or processing system. The processors for the neural network may be general purpose processors, or may be special purpose processors designed specifically for neural network computing.

While some example embodiments are discussed in connection with a neural network, example embodiments presented herein are not limited thereto and may also be applied to other types or forms of computing and/or processing systems, such as Bayesian-based computing systems, support vector machines, Adaboost-based computing systems, conventional computer systems, supercomputers, quantum computers, and the like.

A neural network used to recognize a gait motion may also be trained based on right and left hip joint angle information, vertical acceleration values, and the like for each of gait motions. Data sensed and/or measured during a gait motion recognition period may be input to the above trained neural network and a gait motion of a user may be recognized. A method of training a neural network for a gait motion will be further described with reference to FIG. 7.

To input data to the neural network, input data may need to have the same length or size. However, data of user's right and left hip joint angle information and acceleration information measured during a gait motion recognition period may have different lengths or sizes.

Accordingly, to input data to the neural network, resampling may be required so that data may have the same length or the same size. The resampling unit 230 may resample data of right and left hip joint angle information, angular velocity information and vertical acceleration information so that the data may have the same size, and may reset the data in a data format used to input the data to the neural network.

For example, when a data format used to input data to a neural network needs to be input in an order of a hip joint angle of a swinging leg, a hip joint angle of a leg stepped on the ground, a hip joint angular velocity of a swinging leg, a hip joint angular velocity of a leg stepped on the ground, and a vertical acceleration, the resampling unit 230 may resample data so that the data may have the same size, may connect the data in the order, may set the data in the data format, may convert the data to a different format, and/or modify the data to comply with any other data requirements or preferences for the network. If, however, the neural network does not require input data to be the same length or size, the resampling operation may be omitted. The resampling unit may be omitted as well, if not required.

The recognition unit 220 may recognize the gait motion by inputting the data resampled by the resampling unit 230 to the trained neural network. However, when all gait motions are recognized using the neural network, a structure of the neural network may be complicated. Additionally, when measured data corresponds to an exceptional or unexpected situation, for example, when a user falls over, it may be difficult to accurately recognize a gait motion.

Hereinafter, a method of recognizing a gait motion using a simplified neural network, instead of recognizing all gait motions using a neural network, will be described. The simplified neural network may be used to recognize a desired (or, alternatively predetermined) gait motion instead of all gait motions.

The recognition unit 220 may not use a neural network to recognize a gait motion that is easily distinguishable through a comparison to a threshold at a desired (or, alternatively predetermined) point. Accordingly, by reducing a number of gait motions to be recognized using the neural network, a structure of the neural network may be simplified. In addition, when measured data corresponds to an exceptional or unexpected situation, a gait motion may be accurately recognized and thus, it is possible to more robustly recognize a gait motion. Further, the recognition unit 220 may include a processor and memory for the recognizing the gait motion information processing, or may use processors included in the setting unit 210, resampling unit 230, or the walking assistance apparatus for the gait motion information processing.

For example, when a vertical acceleration value at a desired and/or preset first point in vertical acceleration information, the vertical acceleration information including vertical acceleration values measured during a gait motion recognition period, is equal to or greater than a first threshold, the recognition unit 220 may recognize a gait motion as walking down stairs.

The first point may refer to a point at which a vertical acceleration value for walking down stairs is detected or distinguished from vertical acceleration values for the other gait motions, and may be set differently based on a set gait motion recognition period. In addition, the first threshold may be set as an arbitrary value between the vertical acceleration value for walking down stairs and the vertical acceleration values for the other gait motions.

For example, when a gait motion recognition period is set for each step or stride, the first point at which the vertical acceleration value for walking down stairs is detected or distinguished from the vertical acceleration values for the other gait motions among vertical acceleration values measured for each step or stride, may exist. When a vertical acceleration value at the first point is equal to or greater than the first threshold by comparing the vertical acceleration value at the first point and the first threshold, the gait motion may be recognized as walking down stairs.

As described above, the recognition unit 220 may easily detect, distinguish and/or recognize walking down stairs from the other gait motions by comparing the vertical acceleration value at the first point and the first threshold, instead of using a neural network.

When the vertical acceleration value at the first point is less than the first threshold, the recognition unit 220 may recognize the gait motion as either walking down a slope or level walking, using the neural network. When the gait motion is recognized using the neural network as described above, resampling may be required so that data measured during a gait motion recognition period may have the same size or format. Resampling of measured data by the resampling unit 230 has been described above.

The recognition unit 220 may input the data resampled by the resampling unit 230 to the trained neural network, and may recognize the gait motion as either walking down a slope or level walking. As described above, the recognition unit 220 may recognize either walking down a slope or level walking, instead of recognizing all gait motions using the neural network and accordingly, the neural network used to recognize a gait motion may be simplified.

In an example, when the gait motion is not recognized as walking down a slope and/or level walking using the neural network, and when an absolute value of a rotational speed in a forward direction at a desired and/or preset second point in rotational speed information, the rotational speed information including rotational speed values in the forward direction measured during the gait motion recognition period is equal to or greater than a second threshold, the recognition unit 220 may recognize the gait motion as walking up stairs.

In another example, when the gait motion is not recognized as walking down a slope and/or level walking using the neural network, and when the absolute value of the rotational speed in the forward direction at the second point is less than the second threshold, the recognition unit 220 may recognize the gait motion as walking up a slope.

As described above, the recognition unit 220 may recognize a gait motion by detecting and/or distinguishing walking down stairs from the other gait motions. Similarly, the recognition unit 220 may recognize walking up stairs and walking up a slope by comparing the second threshold to the absolute value of the rotational speed in the forward direction at the second point.

The second point may refer to a point at which an absolute value of a rotational speed in the forward direction for walking up stairs is detected and/or distinguished from an absolute value of a rotational speed in the forward direction for walking up a slope, and may be set differently based on a set gait motion recognition period. Additionally, the second threshold may be set as an arbitrary value between the absolute values of the rational speed in the forward direction for walking up stairs and walking up a slope.

As described above, the recognition unit 220 may easily distinguish walking up stairs from walking up a slope by comparing the second threshold to the absolute value of the rotational speed in the forward direction at the second point, instead of using the neural network.

The recognition unit 220 may easily recognize at least one gait motion through a comparison to a desired and/or preset threshold at a desired (or, alternatively predetermined) point, instead of using the neural network to recognize all gait motions. Therefore, it is possible to reduce complexity of the neural network, and to more robustly recognize a gait motion.

Additionally, the recognition unit 220 may transmit information based on the recognized gait motion to a walking assistance apparatus to improve and/or optimize the assistance provided by the walking assistance apparatus to the user. The apparatus 200 may engage in bi-directional, or mono-directional, communications with a walking assistance apparatus, such as walking assistance apparatus 100. The communications may occur over a wired connection, such as via a bus interface, fiber optic connection, or Ethernet, etc. The apparatus 200 may also communicate with the walking assistance apparatus or a wireless connection, such as WiFi, Bluetooth, GSM, CDMA, LTE, RF, infrared, microwave, etc. Further, the apparatus 200 may be coupled to and/or integrated into a walking assistance apparatus. For example, the setting unit, recognition unit, and/or resampling unit may be integrated into various components of a walking assistance apparatus itself, such as the driver 100, the sensor 120, the IMU sensor 130, and/or the controller 140.

Figure 3:
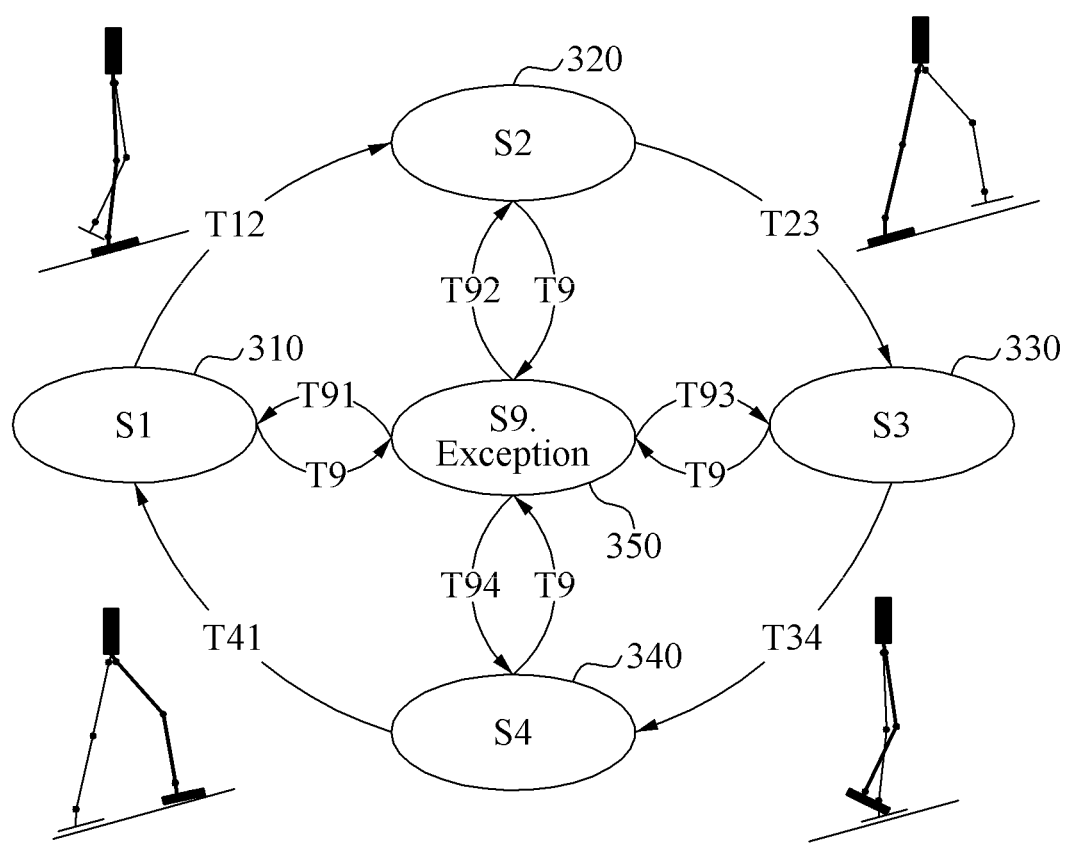
FIG. 3 illustrates a finite state machine (FSM) to set a gait motion recognition period according to some example embodiments.

FIG. 3 illustrates a FSM to set a gait motion recognition period according to some example embodiments.

In FIG. 3, the setting unit 210 of FIG. 2 may set a gait motion recognition period, using an FSM including states based on a gait cycle. A transition condition included in the FSM may be set based on right and left hip joint angles and/or right and left hip joint angular velocities at points at which the right and left hip joint angles and/or the right and left hip joint angular velocities cross. Information on the right and left hip joint angles based on the transition condition may be set, for example, as shown in Table 1.

TABLE 1

| T41: S4-> S1 | T12: S1->S2 | T23: S2->S3 | T34: S3->S4 |
|---|---|---|---|
| Previous state: S4, dq_r < dq_l | Previous state: S1, q_l > q_r | Previous state: S2, dq_r > dq_l | Previous state: S3, q_r > q_l |

In Table 1, T41 represents a transition condition from a state S4 340 to a state S1 310, and T12 represents a transition condition from the state S1 310 to a state S2 320. T23 represents a transition condition from the state S2 320 to a state S3 330, and T34 represents a transition condition from the state S3 330 to the state S4 340.

Additionally, q_l denotes a left hip joint angle, q_r denotes a right hip joint angle, dq_l denotes a left hip joint angular velocity, and dq_r denotes a right hip joint angular velocity.

In the state S1 310, a swinging right leg lands while a left leg remains standing. When an event in which the right leg and the left leg cross occurs in the state S1 310, the state S1 310 may transition to the state S2 320 in which the left leg swings while the right leg remains standing.

The event in which the right leg and the left leg cross may occur when the left leg swings while the right leg remains standing. Accordingly, due to an increase in a left hip joint angle, the left hip joint angle and a right hip joint angle may cross. As shown in Table 1, a transition condition in which the left hip joint angle is higher than the right hip joint angle may be set.

In the state S2 320, the left leg swings while the right leg remains standing. When an event to stop the swing of the left leg occurs in the state S2 320, the state S2 320 may transition to the state S3 330 in which the left leg swinging lands while the right leg remains standing.

The event to stop the swing of the left leg may occur when the left leg lands. Accordingly, due to a decrease in a left hip joint angular velocity, the left hip joint angular velocity and a right hip joint angular velocity may cross. As shown in Table 1, a transition condition in which the right hip joint angular velocity is higher than the left hip joint angular velocity may be set.

In the state S3 330, the swinging left leg lands while the right leg remains standing. When an event in which the right leg and the left leg cross occurs in the state S3 330, the state S3 330 may transition to the state S4 340 in which the right leg swings while the left leg remains standing.

The event in which the right leg and the left leg cross may occur when the right leg swings while the left leg remains standing. Accordingly, due to an increase in a right hip joint angle, the right hip joint angle and the left hip joint angle may cross. As shown in Table 1, a transition condition in which the right hip joint angle is higher than the left hip joint angle may be set.

In the state S4 340, the right leg swings while the left leg remains standing. When an event to stop the swing of the right leg occurs in the state S4 340, the state S4 340 may transition to the state S1 310.

The event to stop the swing of the right leg may occur when the right leg lands. Accordingly, due to a decrease in the right hip joint angular velocity, the right hip joint angular velocity and the left hip joint angular velocity may cross. As shown in Table 1, a transition condition in which the left hip joint angular velocity is higher than the right hip joint angular velocity may be set.

As described above, a left step may be caused by a transition to the states S2 320 and S3 330, and a right step may be caused by a transition to the states S4 340 and S1 310. Accordingly, for example, every time a state transition is performed twice, a gait motion recognition period may be set for each step.

Additionally, the right step and the left step may be caused by all transitions to the states S1 310 through S4 340 occur, the right step and the left step. Accordingly, for example, every time a state transition is performed four times, a gait motion recognition period may be set for each stride.

When a difference between a right hip joint angle and a left hip joint angle, and a difference between a right hip joint angular velocity and a left hip joint angular velocity are equal to less than a desired (or, alternatively predetermined) threshold, or when a period of time in which each state is maintained is equal to or greater than a desired (or, alternatively predetermined) period of time, a situation T9 in which walking stops or an exceptional situation may be recognized, and a transition to an exception state S9 350 may be performed.

As shown in FIG. 3, all states may transition to the exception state S9 350. When transition conditions T91, T92, T93, and T94 to transition from the exception state S9 350 to the states S1 310 through S4 340 are satisfied, the exception state S9 350 may transition to each of the states S1 310 through S4 340.

The setting unit 210 may set the gait motion recognition period, using the FSM, as described above. However, the gait motion recognition period may not need to be set for each step or stride. For example, based on user's settings, the gait motion recognition period may be set every time a state transition is performed once, twice, or three times, etc.

Figure 4:
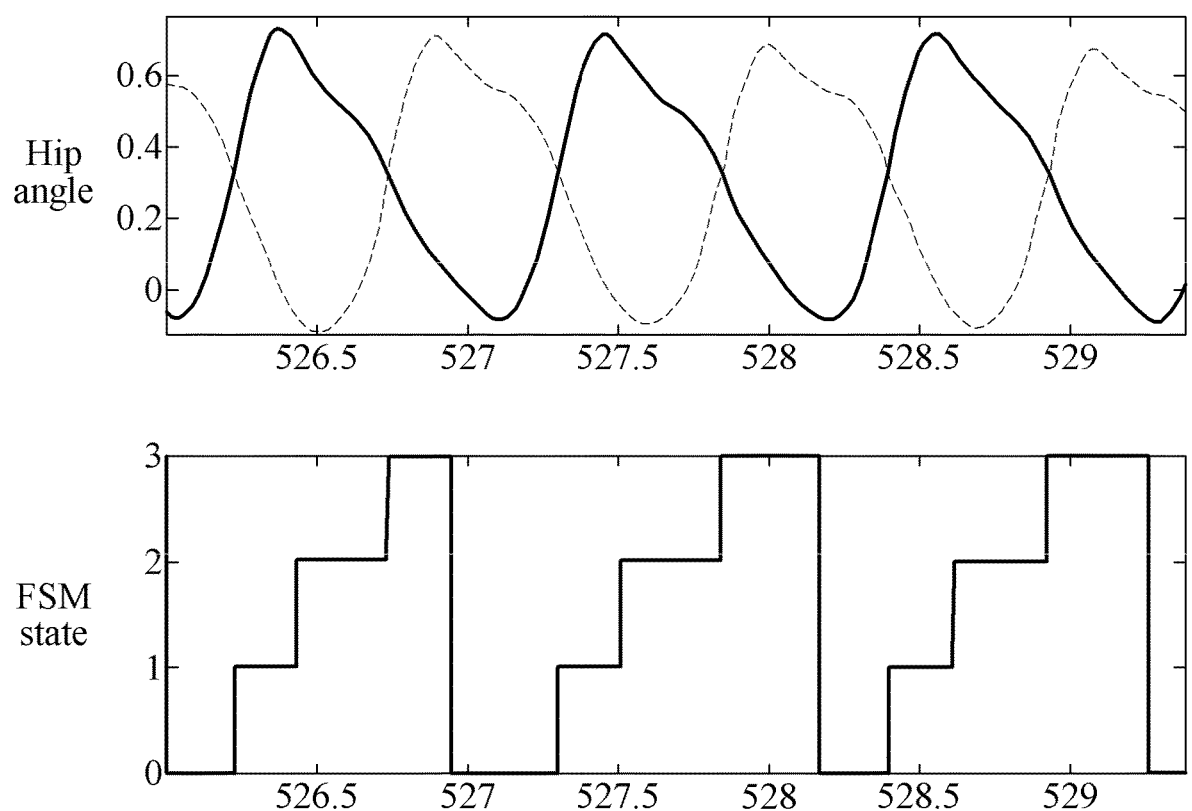
FIG. 4 illustrates a relationship between a hip joint angle and states included in an FSM according to some example embodiments.

FIG. 4 illustrates a relationship between a hip joint angle and states included in an FSM according to some example embodiments.

FIG. 4 shows a graph of hip joint angles based on a gait motion, and a graph of state transitions based on the FSM. For the graph of the hip joint angles based on a gait motion, the solid line of the graph corresponds to a first leg while the dotted line corresponds to a second leg. For example, a hip joint angle may increase by swinging a leg until a point in time at which the swinging leg lands.

Additionally, when a swinging leg lands and remains standing and the other leg swings, the hip joint angle of the landing leg may decrease. Similarly, the hip joint angle of the landing leg may decrease until a point in time at which the other swinging leg lands on the ground.

In the FSM, a transition between states may be performed at a point at which a right hip joint angle and a left hip joint angle cross, and a point at which a right hip joint angular velocity and a left hip joint angular velocity cross, as described above with reference to FIG. 3. As shown in the FSM graph of FIG. 4, a transition between states may be performed at each point at which a right leg angle and a left leg angle cross, and each point at which a right leg angular velocity and a left leg angular velocity cross.

Figure 5:
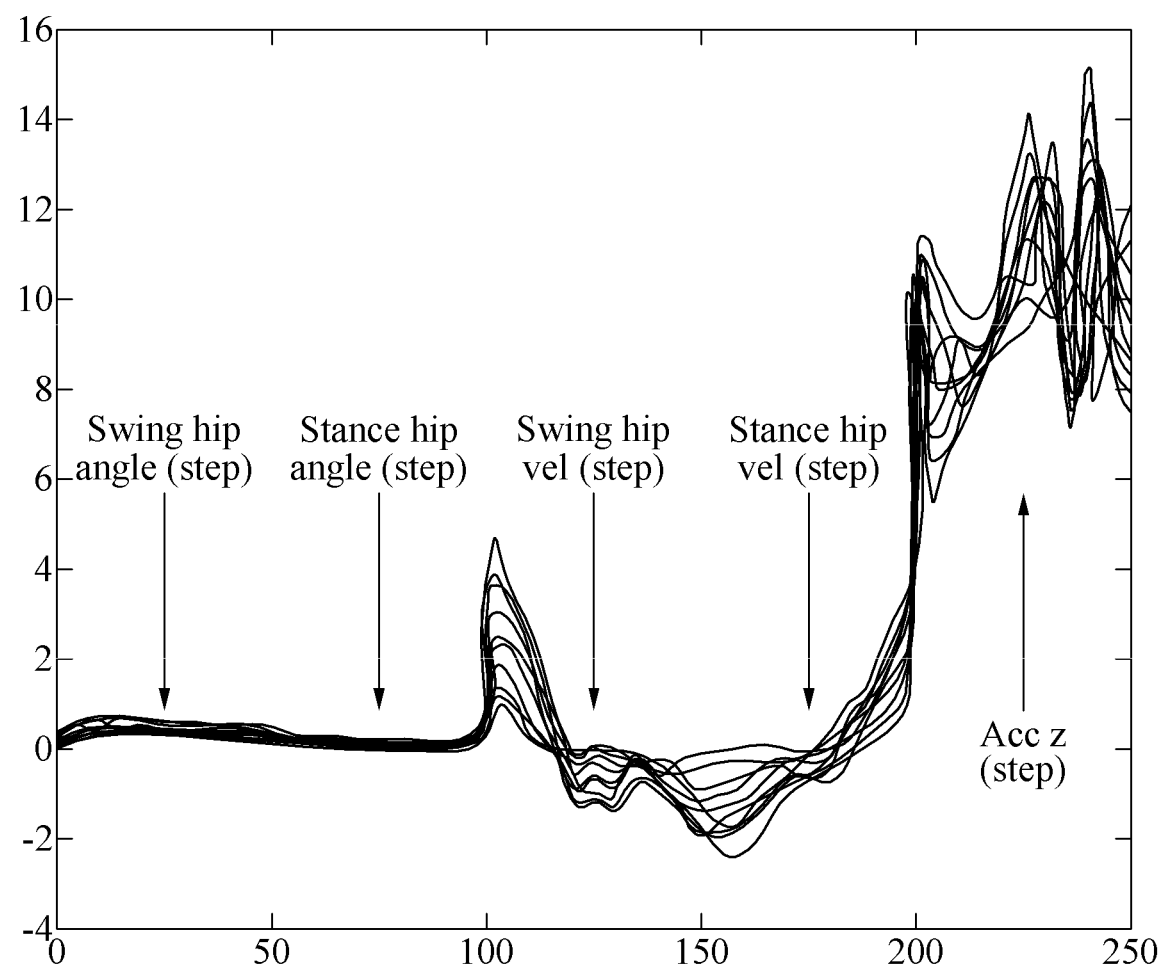
FIG. 5 illustrates data resampled to be input to a neural network according to some example embodiments.

FIG. 5 illustrates data resampled to be input to a neural network according to some example embodiments.

Referring to FIG. 5, the resampling unit 230 of FIG. 2 may resample data of right and left hip joint angle information, angular velocity information and vertical acceleration information measured during a gait motion recognition period so that the data may have the same size, and may reset the resampled data in a data format used to input the data to the neural network. The resampling unit 230 may include a processor and memory for the resampling of the right and left hip joint angle information data, or may use processors included in the setting unit 210, recognition unit 220, or the walking assistance apparatus for the resampling of the right and left hip joint angle information data.

As described above, to input data to the neural network, the input data may need to have the same length or the same size. However, because data of user's right and left hip joint angle information and acceleration information measured during a gait motion recognition period may have different lengths, resampling may be required so that the data may have the same length or the same size.

As shown in FIG. 5, the data format may be set in an order of a hip joint angle of a swinging leg, a hip joint angle of a standing leg, a hip joint angular velocity of a swinging leg, a hip joint angular velocity of a standing leg, and a vertical acceleration.

To input measured data to the neural network, the resampling unit 230 may resample the data so that the data may have the same length or the same size, may connect the data in the order, may set the data in the data format, may convert the data to a different format, and/or modify the data to comply with any other data requirements or preferences for the network.

For example, in FIG. 5, the data may be resampled so as to have the same length corresponding to 50 pieces of data during the gait motion recognition period, and the data format may include a total of 250 pieces of data connected in the order.

However, the data format of FIG. 5 is merely an example for description of the example embodiments, and there is no limitation thereto. Accordingly, it should be obvious to one of ordinary skill in the art that the data format may be changed based on a process of training the neural network.

The recognition unit 220 of FIG. 2 may recognize a gait motion of a user, based on the data resampled and set in the data format by the resampling unit 230.

Figure 6:
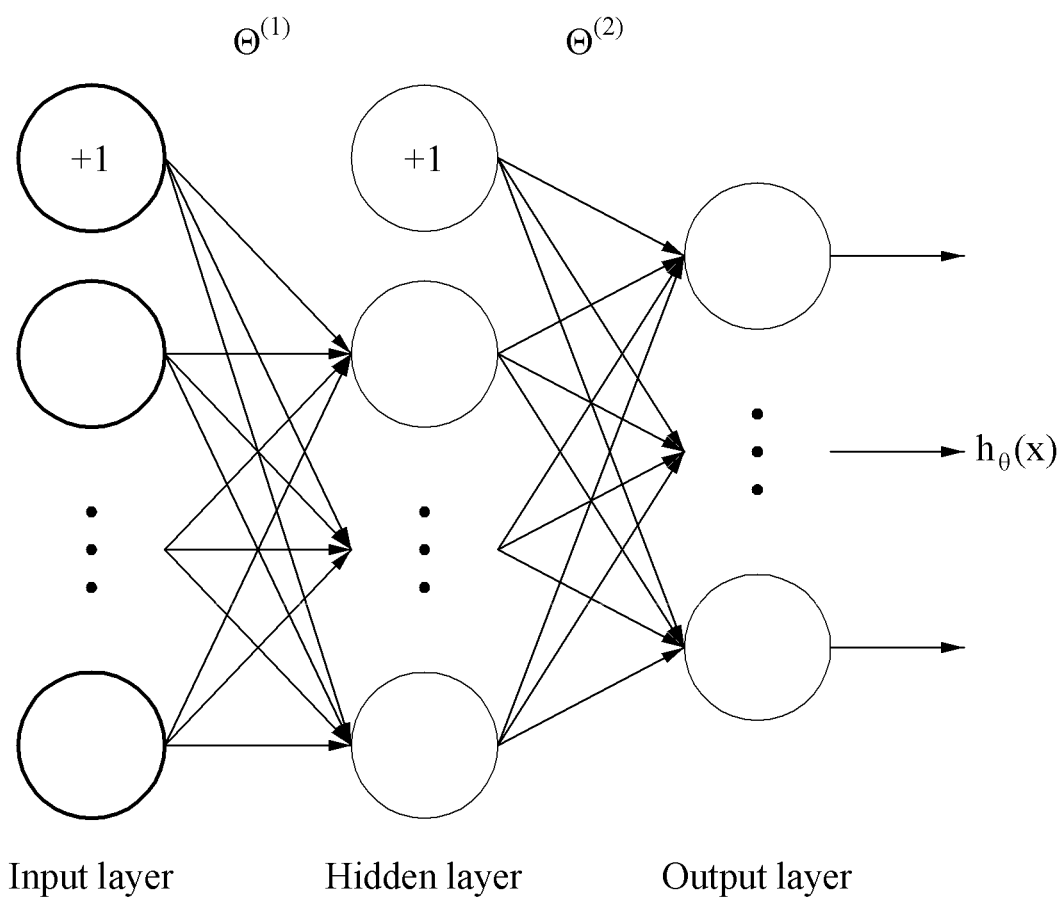
FIG. 6 illustrates a neural network according to some example embodiments.

FIG. 6 illustrates a neural network according to some example embodiments.

FIG. 6 illustrates an example of a neural network to recognize a gait motion. The neural network of FIG. 6 may be simplified to recognize either walking down a slope or level walking, instead of recognizing all gait motions.

The neural network of FIG. 6 may be a three-layer model, and may include an input layer, a hidden layer, and an output layer. The input layer may receive an input of the 250 pieces of resampled data in FIG. 5, and the output layer may distinguish and output gait motions, for example walking down a slope, level walking, and the other gait motions.

Data input through the input layer may be multiplied by connection strengths of connection lines between the input layer and hidden layer, and may be input to the hidden layer. An operation may be performed on the data input to the hidden layer, and the data may be output to the output layer. The data output from the hidden layer may be multiplied by connection strengths of connection lines between the hidden layer and the output layer, and may be input to the output layer. An operation may be performed on the data input to the output layer, and the data may be output.

The input layer, the hidden layer, and the output layer may be referred to as neurons or nodes, and the connection strengths of the connection lines between the input layer and hidden layer and the connection strengths of the connection lines between the hidden layer and the output layer may be referred to as connection weights, or densities of the connection lines.

A connection strength may refer to a desired (or, alternatively predetermined) value of each of the connection lines, and data passing through a connection line may be multiplied by a connection strength of the connection line. The input layer may refer to a neuron to which input data to be classified is input, and the hidden layer may refer to a neuron to perform an operation on an input value and to solve a nonlinear problem. The output layer may refer to a neuron to output data corresponding to input data.

A connection strength of a connection line connecting layers may have a value set during a process of training the neural network. Accordingly, during the process of training the neural network, connection strengths $\theta 1$ and $\theta 2$ of connection lines may be set based on data values for each gait motion.

The simplified neural network of FIG. 6 used to distinguish walking down a slope or level walking from the other gait motions and to output the gait motions is merely an example for description of the example embodiments, and there is no limitation thereto. Additionally, it should be obvious to one of ordinary skill in the art that a neural network including a larger number of hidden layers may be used to recognize all gait motions.

In comparison to a neural network used to recognize all gait motions, the simplified neural network of FIG. 6 may be used, instead of using a neural network used to recognize a gait motion that is easily distinguishable from the other gait motions through a comparison to a threshold at a desired (or, alternatively predetermined) point.

Figure 7:
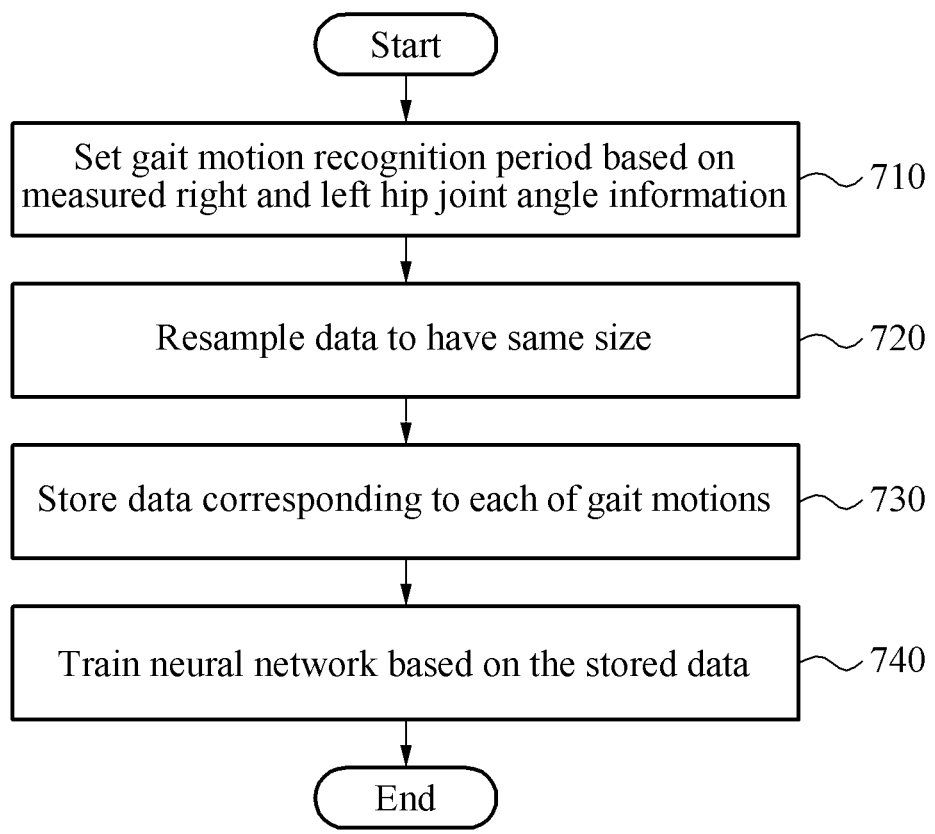
FIG. 7 is a flowchart illustrating a method of training a neural network according to some example embodiments.

FIG. 7 is a flowchart illustrating a method of training a neural network according to some example embodiments.

Referring to FIG. 7, in operation 710, a gait motion recognition period may be set based on measured right and left hip joint angle information. In a process of training a neural network, a gait motion recognition period may need to be set, similar to a process of recognizing a gait motion.

The neural network may be trained based on right and left hip joint angle information and a vertical acceleration value for each gait motion, to recognize a gait motion. The process of training the neural network may be performed based on the above-described data measured during the gait motion recognition period and accordingly, the gait motion recognition period may need to be set.

In operation 720, data measured during the gait motion recognition period may be resampled so as to have the same size. In the process of training the neural network, input data may need to have the same length. However, data of user's right and left hip joint angle information and acceleration information measured during a gait motion recognition period may have different lengths.

Accordingly, to train the neural network, resampling may be required so that data may have the same length or the same size, in the same manner as using a neural network to recognize a gait motion. The resampling unit 230 may resample data of right and left hip joint angle information, angular velocity information and vertical acceleration information measured during the gait motion recognition period so that the data may have the same size, and may reset the data in a data format used to train the neural network.

In operation 730, data measured corresponding to each of gait motions may be stored. To train the neural network, the measured data may be resampled in operation 720. In other words, the resampled data may be stored, to train the neural network.

For example, resampled data at an i-th step and a gait motion at the i-th step may be associated with each other and stored. Accordingly, resampled data and a gait motion for each step may be associated with each other, stored, and used to train the neural network.

In operation 740, the neural network may be trained based on the stored data. In the process of training the neural network, a connection strength of each of connection lines may be set based on data values for each gait motion.

Additionally, the neural network may be trained differently based on a number of gait motions to be recognized through the neural network. For example, the neural network may be trained to recognize all gait motions, or to recognize a desired (or, alternatively predetermined) gait motion.

As described above, a simplified neural network may be trained to recognize a gait motion that is easily distinguishable from the other gait motions through a comparison to a threshold at a desired (or, alternatively predetermined) point, instead of using a neural network used to recognize all gait motions.

Figure 8:
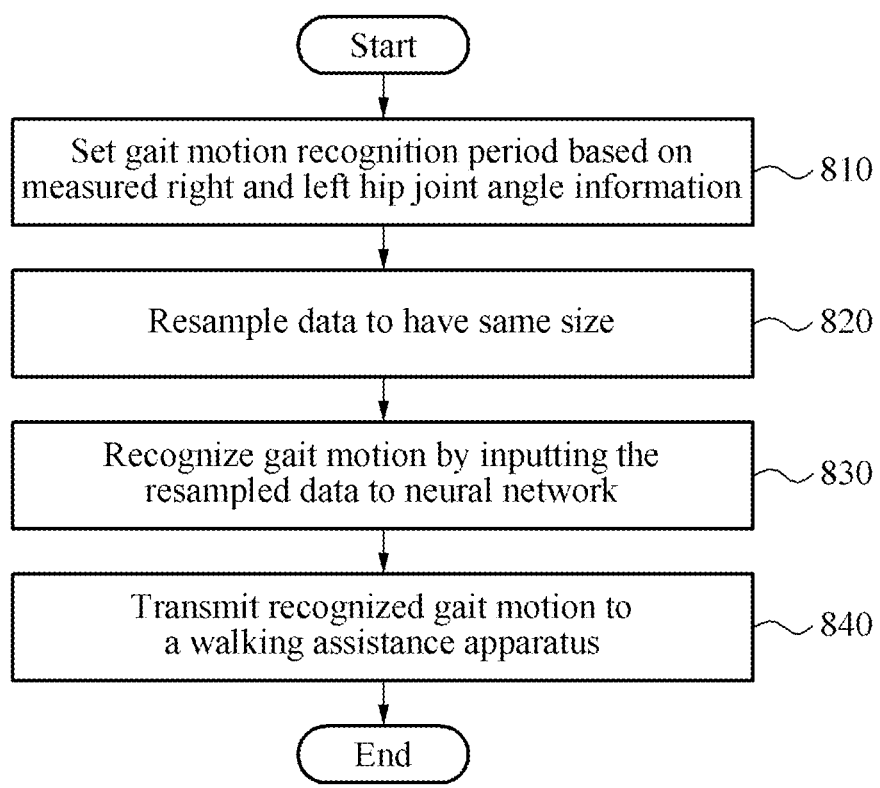
FIG. 8 is a flowchart illustrating an example of a method of recognizing a gait motion according to some example embodiments.

FIG. 8 is a flowchart illustrating an example of a method of recognizing a gait motion according to some example embodiments. The method of FIG. 8 may be performed by the apparatus 200 of FIG. 2.

Referring to FIG. 8, in operation 810, the setting unit 210 may set a gait motion recognition period, based on measured right and left hip joint angle information. The gait motion recognition period may refer to a period used to recognize a gait motion of a user, and a user's motion may be recognized based on data measured during the set gait motion recognition period.

The setting unit 210 may set the gait motion recognition period, using an FSM including states based on a gait cycle. A transition condition between the states in the FSM may be set based on right and left hip joint angles and/or right and left hip joint angular velocities at points at which the right and left hip joint angles and/or the right and left hip joint angular velocities cross.

In operation 820, the resampling unit 230 may resample data of right and left hip joint angle information, angular velocity information and vertical acceleration information so that the data may have the same size, and may reset the data in a data format to input the data to a neural network. The right and left hip joint angle information, the angular velocity information and the vertical acceleration information may be measured during the gait motion recognition period.

In operation 830, the recognition unit 220 may recognize a gait motion by inputting the data resampled by the resampling unit 230 to a trained neural network. The gait motion may include, for example, level walking, walking up stairs, walking down stairs, walking up a slope and walking down a slope.

In operation 840, the recognition unit 220 may transmit the results of the recognition operation to a walking assistance apparatus, such as the walking assistance apparatus in FIG. 1, in order to provide improved and/or optimized walking assistance to the user based on the recognized gait motion of the user.

Figure 9:
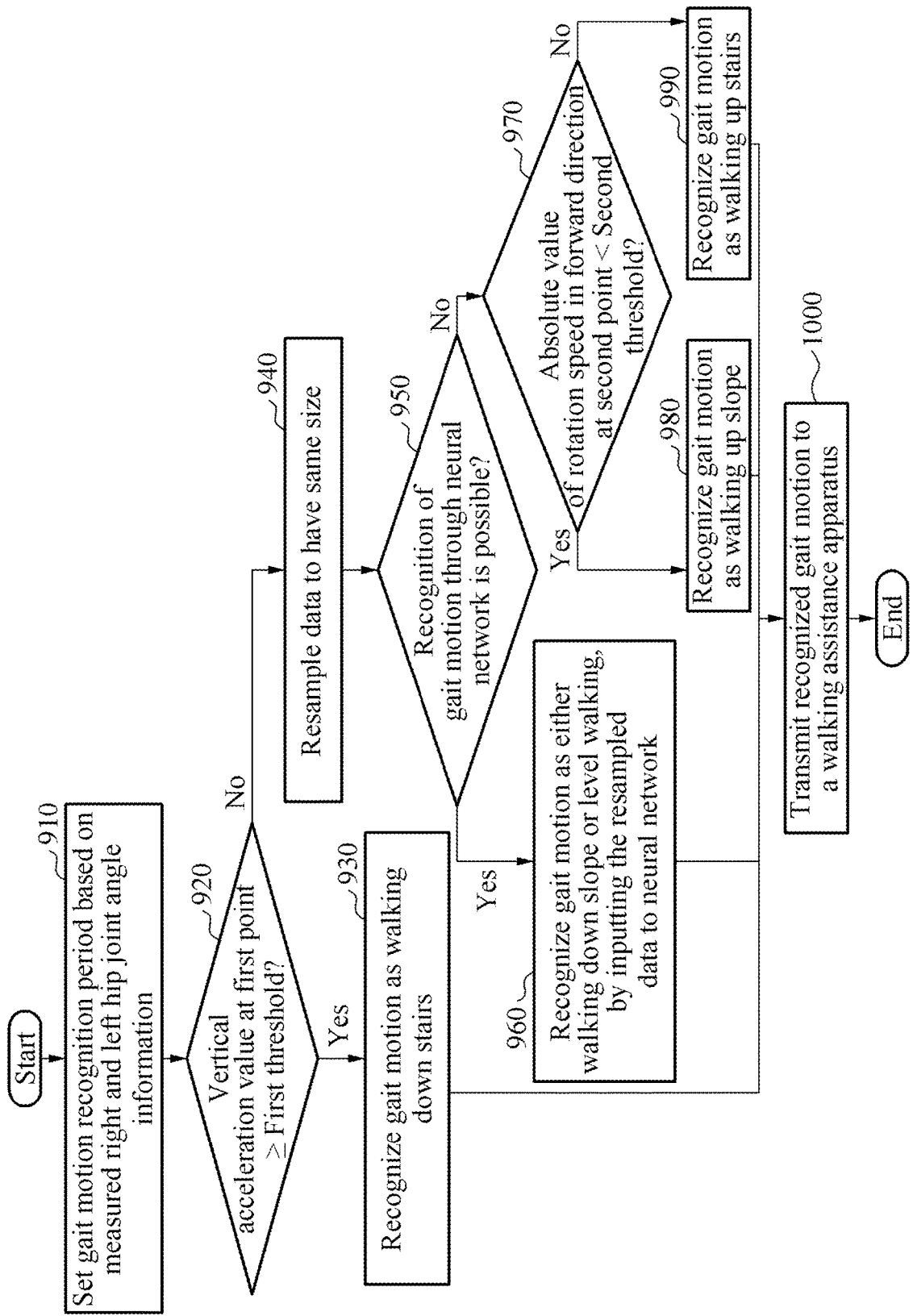
FIG. 9 is a flowchart illustrating another example of a method of recognizing a gait motion according to some example embodiments.

FIG. 9 is a flowchart illustrating another example of a method of recognizing a gait motion according to some example embodiments. The method of FIG. 9 may also be performed by the apparatus 200 of FIG. 2.

Referring to FIG. 9, in operation 910, the setting unit 210 may set a gait motion recognition period based on measured right and left hip joint angle information. The gait motion recognition period may refer to a period used to recognize a gait motion of a user, and a user's motion may be recognized based on data measured during the set gait motion recognition period.

In operation 920, the recognition unit 220 may compare a first threshold to a vertical acceleration value at a desired and/or preset first point in vertical acceleration information including vertical acceleration values measured during the gait motion recognition period. The first point may refer to a point at which a vertical acceleration value for walking down stairs is detectable or distinguished from vertical acceleration values for the other gait motions, and may be set differently based on a set gait motion recognition period. In addition, the first threshold may be set as an arbitrary value between the vertical acceleration value for walking down stairs and the vertical acceleration values for the other gait motions.

When the vertical acceleration value at the first point is equal to or greater than the first threshold, the recognition unit 220 may recognize a gait motion as walking down stairs in operation 930.

When the vertical acceleration value at the first point is less than the first threshold, the resampling unit 230 may resample data of right and left hip joint angle information, angular velocity information and vertical acceleration information so that the data may have the same size, and may reset the data in a data format to input the data to a neural network in operation 940. The right and left hip joint angle information, the angular velocity information and the vertical acceleration information may be measured during the gait motion recognition period.

In operation 950, the recognition unit 220 may determine whether recognition of a gait motion through the neural network is possible. In an example, when all gait motions are recognized through the neural network, a structure of the neural network may be complicated. In another example, when measured data corresponds to an exceptional situation, it may be difficult to accurately recognize a gait motion.

Accordingly, the recognition unit 220 may use a simplified neural network to recognize a desired (or, alternatively predetermined) gait motion, instead of using a neural network to recognize all gait motions.

In operation 960, the recognition unit 220 may recognize a gait motion as either walking down a slope or level walking, by inputting the data resampled by the resampling unit 230 to a trained neural network.

As described above, the recognition unit 220 may recognize either walking down a slope or level walking using the neural network, instead of recognizing all gait motions. Thus, the neural network used to recognize a gait motion may be simplified.

When the gait motion is not recognized as walking down a slope and level walking using the neural network, the recognition unit 220 may compare a second threshold to an absolute value of a rotational speed in a forward direction at a desired and/or preset second point in rotational speed information including rotational speed values in the forward direction measured during the gait motion recognition period in operation 970.

When the absolute value of the rotational speed in the forward direction at the second point is less than the second threshold, the recognition unit 220 may recognize the gait motion as walking up a slope in operation 980.

When the absolute value of the rotational speed in the forward direction at the second point is equal to or greater than the second threshold, the recognition unit 220 may recognize the gait motion as walking up stairs in operation 990.

The second point may refer to a point at which an absolute value of a rotational speed in the forward direction for walking up stairs is detected or distinguished from an absolute value of a rotational speed in the forward direction for walking up a slope, and may be set differently based on a set gait motion recognition period. Additionally, the second threshold may be set as an arbitrary value between the absolute values of the rational speed in the forward direction for walking up stairs and walking up a slope.

In operation 1000, the recognized gait motion may be transmitted to a walking assistance apparatus, such as the walking assistance apparatus in FIG. 1, in order to provide improved and/or optimized walking assistance to the user based on the recognized gait motion of the user.

The units and/or modules described herein may be implemented using hardware components, software components, or a combination thereof. For example, the hardware components may include microphones, amplifiers, band-pass filters, audio to digital converters, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of some example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

It should be understood that example embodiments described herein should be considered in a descriptive sense only and not for purposes of limitation. Descriptions of features or aspects within each device or method according to example embodiments should typically be considered as available for other similar features or aspects in other devices or methods according to example embodiments. While some example embodiments have been particularly shown and described, it will be understood by one of ordinary skill in the art that variations in form and detail may be made therein without departing from the spirit and scope of the claims.

What is claimed is:

1. A method of recognizing a gait motion, the method comprising:
    setting, by at least one processor coupled to a walking assistance apparatus, a gait motion recognition period based on measured right and left hip joint angle information;
    determining, by the at least one processor, whether a vertical acceleration value measured during the gait motion recognition period is equal to or greater than a first threshold at a first point to determine when to use a trained neural network for the gait motion recognition, the first point is a predetermined point of the gait motion recognition period so that walking down stairs and other gait motions are distinguished based on values of vertical acceleration;
    determining, by the at least one processor, a first gait motion as walking down stairs without use of the trained neural network, when the vertical acceleration value at the first point is equal to or greater than the first threshold;
    determining, by the at least one processor, a second gait motion by inputting the right and left hip joint angle information and the vertical acceleration value to the trained neural network when the vertical acceleration value at the desired first point is less than the first threshold; and
    providing, by the at least one processor, information to the walking assistance apparatus based on results of the setting and the first gait motion or the second gait motion, the information causing the walking assistance apparatus to optimize assistance provided by the walking assistance apparatus to a user.

2. The method of claim 1, further comprising:
    resampling, by the at least one processor, data of the right and left hip joint angle information and a vertical acceleration information in accordance with a data format when the vertical acceleration value is less than the first threshold, the right and left hip joint angle information being measured during the gait motion recognition period.

3. The method of claim 2, further comprising:
    determining, by the at least one processor, the second gait motion as either walking down a slope or level walking, by inputting the resampled data to the trained neural network.

4. The method of claim 3, further comprising:
    determining, by the at least one processor, the second gait motion as walking up stairs,
        when the second gait motion is not determined as walking down a slope or level walking through the trained neural network, and
        when a value of a rotational speed in a forward direction at a desired second point in rotational speed information, the rotational speed information including rotational speed values in the forward direction measured during the gait motion recognition period, is equal to or greater than a second threshold.

5. The method of claim 3, further comprising:
determining, by the at least one processor, the second gait motion as walking up a slope,
when the second gait motion is not determined as walking down a slope or level walking through the trained neural network, and
when a value of a rotational speed in a forward direction at a desired second point in rotational speed information, the rotational speed information including rotational speed values in the forward direction measured during the gait motion recognition period is less than a second threshold.

6. The method of claim 1, wherein the setting comprises setting the gait motion recognition period using a finite state machine (FSM), the FSM including states based on a gait cycle.

7. The method of claim 6, wherein a transition condition between the states is based on right and left hip joint angles or right and left hip joint angular velocities.

8. A method of recognizing a gait motion, the method comprising:
setting, by at least one processor coupled to a walking assistance apparatus, a gait motion recognition period based on measured right and left hip joint angle information;
determining, by the at least one processor, whether a vertical acceleration value measured during the gait motion recognition period is equal to or greater than a first threshold at a first point to determine when to use a trained neural network to be used for the gait motion recognition, the first point is a predetermined point of the gait motion recognition period so that walking down stairs and other gait motions are distinguished based on values of vertical acceleration;
determining, by the at least one processor, a first gait motion as walking down stairs without use of the trained neural network, when the vertical acceleration value at the first point is equal to or greater than the first threshold;
determining, by the at least one processor, a second gait motion by inputting right and left hip joint angle information and the vertical acceleration value to a trained neural network when the vertical acceleration value at the first point in vertical acceleration information is less than the first threshold; and
providing, by the at least one processor, information to the walking assistance apparatus based on results of the setting and the second gait motion, the information causing the walking assistance apparatus to optimize assistance provided by the walking assistance apparatus to a user.

9. The method of claim 8, further comprising:
resampling, by the at least one processor, data of the right and left hip joint angle information and the vertical acceleration information in accordance with a data format.

10. The method of claim 8, wherein the setting comprises setting the gait motion recognition period using a finite state machine (FSM), the FSM including states based on a gait cycle.

11. The method of claim 10, wherein a transition condition between the states is based on right and left hip joint angles or right and left hip joint angular velocities.

12. The method of claim 8, wherein the second gait motion comprises level walking, walking up stairs, walking up a slope, and walking down a slope.

13. An apparatus for recognizing a gait motion, the apparatus comprising:
at least one processor coupled to a walking assistance apparatus, the at least one processor configured to:
set a gait motion recognition period based on measured right and left hip joint angle information,
determine whether a vertical acceleration value measured during the gait motion recognition period is equal to or greater than a first threshold at a first point to determine when to use a trained neural network for the gait motion recognition, the first point is a predetermined point of the gait motion recognition period so that walking down stairs and other gait motions are distinguished based on values of vertical acceleration,
determine a first gait motion as walking down stairs without use of the trained neural network, when the vertical acceleration value at the first point is equal to or greater than the first threshold,
determine a second gait motion by inputting the right and left hip joint angle information and the vertical acceleration value to the trained neural network when the vertical acceleration value at the first point is less than the first threshold, and
provide information to the walking assistance apparatus based on results of the setting and the first gait motion or the second gait motion, the information causing the walking assistance apparatus to optimize assistance provided by the walking assistance apparatus to a user.

14. The apparatus of claim 13, wherein the at least one processor is further configured to:
resample data of right and left hip joint angle information and a vertical acceleration information in accordance with a data format when the vertical acceleration value is less than the first threshold, the right and left hip joint angle information being measured during the gait motion recognition period.

15. The apparatus of claim 13, wherein the at least one processor is further configured to:
recognize the second gait motion as either walking down a slope or level walking by inputting the resampled data to the trained neural network.

16. The apparatus of claim 15, wherein the at least one processor is further configured to:
recognize the second gait motion as walking up stairs,
when the second gait motion is not recognized as walking down a slope or level walking through the trained neural network, and
when a value of a rotational speed in a forward direction at a desired second point in rotational speed information, the rotational speed information including rotational speed values in the forward direction measured during the gait motion recognition period, is equal to or greater than a second threshold.

17. The apparatus of claim 15, wherein the at least one processor is further configured to:
recognize the second gait motion as walking up a slope,
when the second gait motion is not recognized as walking down a slope or level walking through the trained neural network, and
when a value of a rotational speed in a forward direction at a desired second point in rotational speed information, the rotational speed information including rotational speed values in the forward direction measured during the gait motion recognition period, is less than a second threshold.

18. The apparatus of claim 13, wherein the at least one processor is further configured to:
set the gait motion recognition period using a finite state machine (FSM), the FSM including states based on a gait cycle.

19. The apparatus of claim 18, wherein a transition condition between the states is set based on right and left hip joint angles or right and left hip joint angular velocities.

20. A non-transitory computer-readable recording medium storing a program, which when executed by a computer, configures the computer to perform the method of claim 1.

* * * * *